United States Patent
Lee et al.

(10) Patent No.: US 7,170,612 B2
(45) Date of Patent: Jan. 30, 2007

(54) SCANNING ULTRASOUND DETECTION DEVICE USING TWO-WAVE MIXING IN PHOTOREFRACTIVE CRYSTAL INTERFEROMETRY

(75) Inventors: Ju-Yi Lee, Taipei (TW); Hsueh-Ching Shih, Sijhih (TW)

(73) Assignee: Industrial Technology Research Institute, Hsinchu (TW)

( * ) Notice: Subject to any disclaimer, the term of this patent is extended or adjusted under 35 U.S.C. 154(b) by 776 days.

(21) Appl. No.: 10/629,765

(22) Filed: Jul. 30, 2003

(65) Prior Publication Data

US 2004/0024314 A1   Feb. 5, 2004

(30) Foreign Application Priority Data

Aug. 2, 2002   (TW) ............................. 91117487 A

(51) Int. Cl.
  *G01B 11/02* (2006.01)
  *G01B 9/02* (2006.01)
  *G01N 21/41* (2006.01)

(52) U.S. Cl. ........................................ 356/502; 73/657

(58) Field of Classification Search .............. 356/35.5, 356/450, 484, 489, 502, 511, 512; 73/657
  See application file for complete search history.

(56) References Cited

U.S. PATENT DOCUMENTS

| | | | | |
|---|---|---|---|---|
| 5,680,212 A | * | 10/1997 | Blouin et al. | 356/458 |
| 5,827,971 A | * | 10/1998 | Hale et al. | 73/657 |
| 6,813,951 B2 | * | 11/2004 | Blouin et al. | 73/643 |
| 6,819,432 B2 | * | 11/2004 | Pepper et al. | 356/498 |

* cited by examiner

*Primary Examiner*—Gregory J. Toatley, Jr.
*Assistant Examiner*—Michael A. Lyons
(74) *Attorney, Agent, or Firm*—Bacon & Thomas, PLLC

(57) ABSTRACT

This invention relates to a scanning ultrasound detection device using two-wave mixing in photorefractive crystal interferometry. An interferometer with two-wave mixing in photorefractive crystal, and cooperates with a confocal lenses module to perform a scan and inspection of the surface of a target. A rotating unit is used for directing a signal beam for detection to be incident upon different locations of the target. The confocal lens module is used to compensate any changes of reflection path caused by the signal beam having different incident angles. Hence, a reflected signal beam and a reference beam can strike on a photo detector.

11 Claims, 2 Drawing Sheets

SCANNING ULTRASOUND DETECTION DEVICE USING TWO-WAVE MIXING IN PHOTOREFRACTIVE CRYSTAL INTERFEROMETRY

BACKGROUND OF THE INVENTION

1. Field of the Invention

The present invention relates to an ultrasound detection device, and more particularly, to a scanning ultrasound device using two-wave mixing in photorefractive crystal interferometry for non-destructive and non-contact inspection.

2. Description of Related Art

The inspection for defects in material structures is always a critical issue for monitoring and controlling quality in the manufacturing industry. In the conventional destructive inspection for defects, the whole package of a tested sample (e.g. an IC for inspection) is destructively taken apart. For example, in the inspection for insufficient solder or short circuit problem in an integrated circuit (IC), the packaged IC has to be dissolved with a corrosive solution, and then, pins of the IC are inspected with a microscope. However, this inspection process is complex, and is disadvantageous to real-time monitor quality assurance on-line.

Recently, the industry has developed a non-destructive inspection system for monitoring and controlling quality. The process for the non-destructive inspection primarily uses X-rays, an ultrasound probe head as well as an ultrasound optical excitation and detection, etc. Especially, the ultrasound optical excitation and detection has become the main stream for developing the non-destructive inspection because of advantages of remote excitation and detection as well as real-time inspection.

A Two-Wave Mixing in PhotoRefractive Crystal interferometer (TWM in PRC) is considered as the core part of the contemporary ultrasound optical detection system. To apply TWM in PRC to the non-destructive inspection by ultrasound in practice, scanning technology has to be adopted. The conventional solution is to displace or re-locate the whole interferometer system to achieve a scanning function. However, additional mechanism is necessary for this conventional solution, and thus, it complicates the inspection system and increases cost in volume production.

Therefore, it is desirable to provide an optical scanning ultrasound device by TWM in PRC to mitigate and/or obviate the aforementioned problems.

SUMMARY OF THE INVENTION

It is an object of the present invention to provide a scanning ultrasound device using TWM in PRC so as to perform a surface scan and detection of an ultrasound wave.

It is another object of the present invention to provide a scanning ultrasound device using TWM in PRC so as to have compact structure, increase system reliability and reduce cost in volume production.

To attain the above objects, a scanning ultrasound device using TWM in PRC according to the present invention comprises a light source, an ultrasound-wave-generating-module and a target. The ultrasound-wave-generating-module generates at least an ultrasound signal to cause the target to bring about ultrasound vibrations. The ultrasound-wave-generating-module includes an interferometer of TWM in PRC for receiving light coming from the light source to generate a signal beam for detecting the ultrasound vibrations of the target and a reference beam having an interference with the signal beam, and a rotating unit for directing the signal beam to be incident upon different locations of the target to result in a scanning motion. The target described herein can be any substrate, package, test object, etc.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
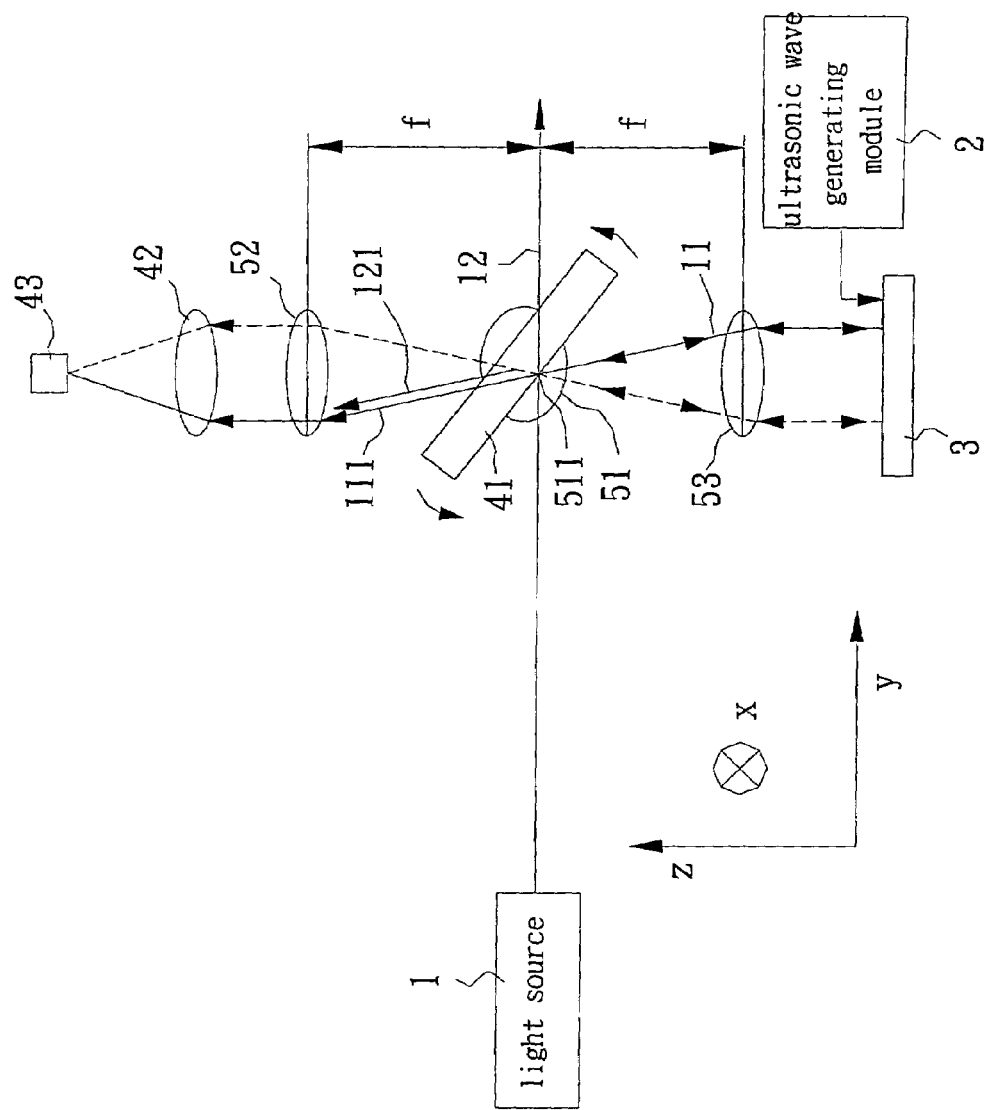
FIG. 1 is a schematic view of a structure of the scanning ultrasound device according to the present invention.

FIG. 1 shows the structure of a preferred embodiment according to the present invention, and provides a schematic view of the structure. The scanning ultrasound device comprises a light source 1, an ultrasound-wave-generating-module 2, a photorefractive crystal 41, a first convex lens 42, a second convex lens 52, a third convex lens 53, a rotating mechanism 51 and a photo detector 43. The photorefractive crystal 41 is supported in the rotating mechanism 51, having a rotation axis 511 where the focal point of the second convex lens 52 and the focal point of the third convex lens 53 are located. The photo detector 43 is mounted at the focal point of the first convex lens 42. As shown in FIG. 1, the first convex lens 42 locates on a position opposed to the focal point of the second convex lens 52 and the focal point of the third convex lens 53. In this embodiment, the light source 1 preferably is a continue wave (CW) laser. When the light source 1 strikes on the photorefractive crystal 41, the light beam reflected by the surface of photorefractive crystal 41 is defined as a signal beam 11 while the light beam passing through the photorefractive crystal 41 is defined as a reference beam 12. A thin optical film may be coated on the surface of the photorefractive crystal 41 to adjust the intensity ratio of the signal beam and the reference beam, if necessary.

Figure 2:
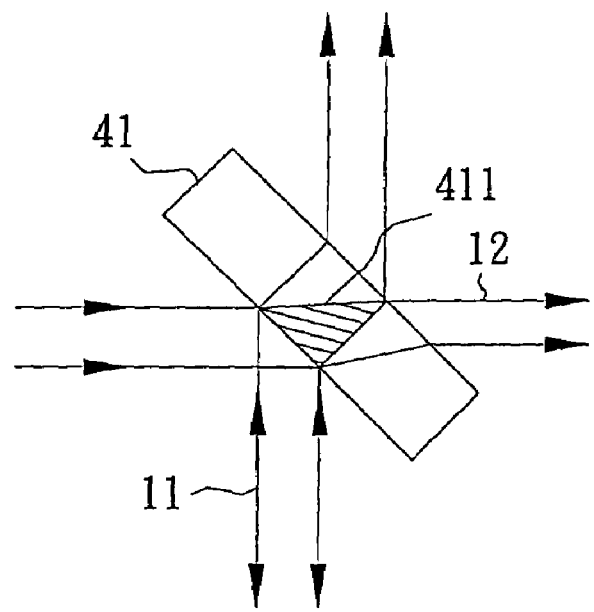
FIG. 2 is a schematic view of a phase grating of a photorefractive crystal according to the present invention.

The signal beam 11 is reflected from the surface of the photorefractive crystal 41, and then strikes on the surface of the test object 3 through the third convex lens 32. Thereafter, the light beam is reflected back from the surface of the test object 3 to the photorefractive crystal 41. The signal beam 11 reflected back to the photorefractive crystal 41 combines with the reference beam 12 to form interference fringe patterns in the photorefractive crystal 41, and then the beam 11 passing through the photorefractive crystal 41 becomes a signal beam 111. The signal beam 111 passing through the photorefractive crystal 41 is further incident on the photo detector 43 through the second convex lens 52 and the first convex lens 42. Because of photorefractive effect, The interference fringe patterns inside the photorefractive crystal 41 generate a phase grating 411. (FIG. 2) The wavefront and wave propagation direction of the diffracted reference beam 121 by means of the phase grating 411 is the same as that of the signal beam 111 passing through the photorefractive crystal 41.

When an ultrasound signal from the ultrasound-wave-generating-module 2 strikes on the test object 3 to cause the ultrasound vibrations of the surface of the test object 3, the frequency of signal beam 11 reflected from the surface of the test object 3 is Doppler shifted by the ultrasonic vibrations. The signal beam 11 for detection passes through the photorefractive crystal 41, and superimposes the diffracted reference beam 121 by means of the photorefractive crystal 41 to generate an interference so that the Doppler shift is demodulated by light intensity thereof. The interfered beam is incident on the photo detector 43 through the convex lenses 52, 42. The photo detector 43 converts the interfered signal into an electrical signal, and then is output to an oscilloscope or a computer apparatus for displaying the inspection results of the test object 3.

In the scanning process, the photorefractive crystal 41 is rotated by means of a rotating mechanism 51 on which the photorefractive crystal 41 is supported to alter the reflection angle of the signal beam 11. The signal beam having a changed reflection angle passes through the third convex lens 53 to be incident on the surface of the test object 3. Because the third convex lens 53 is focused on the rotation axis 511 of the rotating mechanism 51, the signal beam 11 passing though the third convex lens 53 will always be incident vertically on the surface of the test object 3. Namely, the signal beam 11 strikes perpendicularly on the surface of the test object 3 through the third convex lens 53. The signal beam 111 reflected back from the surface of the test object 3 is incident on the rotation axis 511 of the rotating mechanism 51. Hence, the signal beam is driven to perform a linear scan of the surface of the test object when the rotating mechanism 51 is rotated in a single-axial direction. In addition, the signal beam 11 is able to perform a two-dimensional surface-wide scan of the test object 3 when the rotating mechanism 51 is rotated in a biaxial direction.

Figure 3:
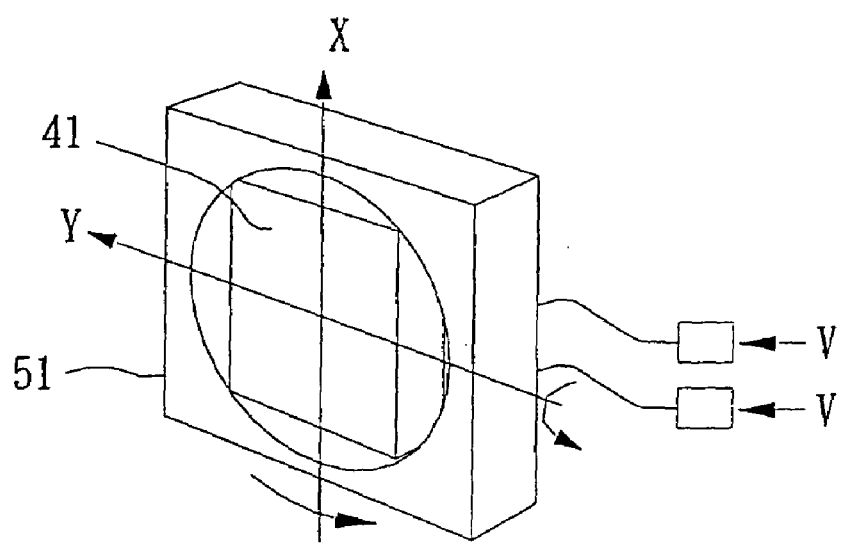
FIG. 3 is a schematic view of a rotating mechanism according to the present invention.

FIG. 3 is a schematic view of a rotating mechanism. In this embodiment, the rotating mechanism 51 can be any single-axial mechanism or biaxial rotating mechanism. For example, the rotating mechanism 51 maybe a motorized kinetic mount driven by a piezoelectric actuator. The photorefractive crystal 41 is supported in the rotating mechanism 51. A voltage (Vx, Vy) is input by a controller driving the piezoelectric actuator so that the photorefractive crystal 41 is rotated around the X-axis or the Y-axis. When the photorefractive crystal 41 is rotated around the X-axis, the signal beam 11 performs a linear scan in a Y-axis direction. When the photorefractive crystal 41 is rotated around the Y-axis, the signal beam 11 performs a linear scan in an X-axis direction. When the photorefractive crystal 41 is rotated around both the X- and the Y-axes, the signal beam performs a two dimensional surface-wide (X-Y) scan.

The aforesaid signal beam 11 is reflected back from the surface of the test object 3 to the photorefractive crystal 41, and passes through the photorefractive crystal 41 to form the signal beam 111. Then, the signal beam 111 enters the second convex lens 52. Because the focal point of the second convex lens 52 is also located at the rotation axis 511, the signal beam 111 passing through the second convex lens 52 will become a parallel beam. The diffracted reference beam 121 by means of the phase grating 411 is parallel to and superimposed on the passed-through signal beam 111 to generate the interference. Subsequently, the beams are focused on the photo detector 43 through the first convex lens 42. The photo detector 43 receives an interfering signal and converts the interfering signal into an electrical signal.

It is understandable from the above description that the present invention adopts the light source, the ultrasound-wave-generating-module, the photorefractive crystal, the convex lens, the confocal convex lenses, the rotating mechanism and the photo detector to inspect the test object in a non-destructive and non-contact manner. Also, the present invention is able to execute a linear scan or a two-dimensional surface-wide scan to have compact structure, increase system reliability and reduce cost in volume production.

Although the present invention has been explained in relation to its preferred embodiment, it is to be understood that many other possible modifications and variations can be made without departing from the spirit and scope of the invention as hereinafter claimed.

What is claimed is:

1. A scanning ultrasound detection device using two-wave mixing in photorefractive interferomtery, in cooperation with a light source, an ultrasound-wave-generating-module and a target wherein said ultrasound-wave-generating-module generates at least an ultrasound signal to cause said target to bring about ultrasound vibrations, comprising:
   an interferometer with two-wave mixing in photorefractive crystal for receiving rays of light coming from said light source to generate a signal beam for detecting said ultrasound vibrations of said target and a reference beam having an interference with said signal beam; and
   a rotating unit for directing said signal beam to be incident upon different locations of said target to result in a scanning motion.

2. The scanning ultrasound detection device of claim 1, wherein said interferometer with two-wave mixing in photorefractive crystal further comprises a photorefractive crystal, a first convex lens, and a photo detector, and the rays of light coming from said light source are incident on said photorefractive crystal; and said signal beam and said reference beam are formed through said photorefractive crystal.

3. The scanning ultrasound detection device of claim 2, wherein said reference beam passes through said photorefractive crystal, and said signal beam is reflected to said target from said photorefractive crystal and then is reflected back to said photorefractive crystal from the surface of said target.

4. The scanning ultrasound detection device of claim 3, wherein said signal beam reflected from the surface of said target brings about a Doppler shift related to ultrasound vibrations of said target; said signal beam passes through said photorefractive crystal, and superimposes a reference beam by means of said photorefractive crystal to generate an interference, and then strikes on said photo detector through said first convex lens.

5. The scanning ultrasound detection device of claim 2, wherein said interferometer with two-wave mixing in photorefractive crystal further comprises a second convex lens and a third convex lens, and said rotating unit has a rotation axis at which the focal point of said second convex lens and the focal point of said third convex lens are located.

6. The scanning ultrasound detection device of claim 5, wherein said photorefractive crystal is supported by said rotating unit, and is rotated by said photorefractive crystal so that said signal beam strikes on said target for scanning of the target.

7. The scanning ultrasound device of claim 6, wherein said rotating unit is rotated in a signal-axial direction.

8. The scanning ultrasound device of claim 6, wherein said rotating unit is rotated in a biaxial direction.

9. The scanning ultrasound detection device of claim 5, wherein said third convex lens for directing said signal beam to be incident perpendicularly on the surface of said target is disposed between said rotation axis and said target; and said second convex lens for altering the direction of said signal beam by means of said photorefractive crystal to become a parallel beam to be focused on said photo detector through said first convex lens is disposed between said rotation axis and said first convex lens.

10. The scanning ultrasound detection device of claim 9, wherein said photo detector is located at the focal point of said first convex lens and is opposed to the side on which said second convex lens is located.

11. The scanning ultrasound detection device of claim 1, wherein said light source is a laser.

* * * * *